United States Patent [19]
Blanche et al.

[11] Patent Number: 6,156,545
[45] Date of Patent: Dec. 5, 2000

[54] BIOSYNTHESIS METHOD ENABLING THE PREPARATION OF COBALAMINS

[75] Inventors: Francis Blanche; Béatrice Cameron, both of Paris; Joël Crouzet, Sceaux; Laurent Debussche, Athis Mons; Denis Thibaut; Elisabeth Remy, both of Paris, all of France

[73] Assignee: Rhone-Poulenc Rorer S.A., Antony, France

[21] Appl. No.: 09/180,582

[22] PCT Filed: May 5, 1997

[86] PCT No.: PCT/FR97/00793

§ 371 Date: Mar. 2, 1999

§ 102(e) Date: Mar. 2, 1999

[87] PCT Pub. No.: WO97/43421

PCT Pub. Date: Nov. 20, 1997

[30] Foreign Application Priority Data

May 13, 1996 [FR] France ................................. 96 05896

[51] Int. Cl.[7] ...................................................... C12P 19/42
[52] U.S. Cl. .................................................................. 435/86
[58] Field of Search ................................................. 435/86

[56] References Cited

PUBLICATIONS

Pollich et al. Identification and Sequence Analysis of Genes Involved in Late Steps of Cobalamin (Vitamin B12) Synthesis in Rhodobacter capsulatus. Journal of Bacteriology (Aug. 1995) 177(15):4481–4487.

Stamford NPJ. Genetics and enzymology of the B12 pathway. Ciba Foundation Symposium (1994) 180:247–266.

Brey et al. Cloning and Multiple Genes Involved with Cobalamin (Vitamin B12) Biosynthesis in *Bacillus megaterium*. Journal of Bacteriology (Aug. 1986) 167(2): 623–630.

Escalante–Semerena et al. The CobII and CobIII Regions of the Cobalamin (Vitamin B12) Biosynthetic Operon of *Salmonella typhimurium* (Jan. 1992) 174(1): 24–29.

*Primary Examiner*—Ponnathapu Achutamurthy
*Assistant Examiner*—Kathleen Kerr
*Attorney, Agent, or Firm*—Finnegan, Henderson, Farabow, Garrett & Dunner, L.L.P.

[57] ABSTRACT

The present invention relates to a biosynthetic process for preparing cobalamines. More precisely, it relates to a process for amplifying the production of cobalamines and, more specifically, of coenzyme $B_{12}$ by means of recombinant DNA techniques and/or by means of adding a novel cobalamine precursor.

12 Claims, 3 Drawing Sheets

BIOSYNTHESIS METHOD ENABLING THE PREPARATION OF COBALAMINS

The present invention relates to a biosynthetic process for preparing cobalamins. More precisely, it relates to a process for amplifying the production of cobalamins and, more specifically, of coenzyme $B_{12}$ by means of recombinant DNA techniques and/or by means of adding a novel cobalamin precursor. Finally, the present invention relates to a process for preparing recombinant strains which are of use in the process for preparing cobalamins according to the present invention.

Vitamin $B_{12}$ is a member of a class of molecules which are termed cobalamins and whose structure is presented, in particular, in WO91/11518.

Cobalamins are synthesized almost exclusively by bacteria in accordance with a complex process which is also described in WO91/11518. Because of the high degree of complexity of the biosynthetic mechanisms, cobalamins, and in particular vitamin $B_{12}$, are principally produced at the industrial level using large-volume cultures of the bacteria *Pseudomonas denitrificans*, *Propionobacterium shermanii* and *Propionobacterium freudenreichii*.

It is widely known that cobalamins are synthesized by certain microorganisms from the following substrates: aminolaevulinic acid, S-adenosyl-L-methionine, cobalt, glutamine, (R)-1-amino-2-propanol and 5,6-dimethylbenzimidazole.

Of the abovementioned precursors, 5,6-dimethylbenzimidazole is synthesized by the microorganisms which produce cobalamins. There appear to exist two biosynthetic pathways for 5,6-dimethyl-benzimidazole: one is characteristic of aerobic microorganisms and involves molecular oxygen while the other is employed by anaerobic microorganisms. Only one gene involved in the anaerobic pathway has been isolated; this is the cobT gene of Salmonella typhimurium (Trzebiatowski et al., 1994). No gene for synthesizing 5,6-dimethylbenzimidazole has to date been identified in the aerobic microorganisms. The quantity of 5,6-dimethylbenzimidazole synthesized by microorganisms is often limiting.

As a consequence, 5,6-dimethylbenzimidazole is prepared chemically and added to the production media. Elimination of this addition to the media would therefore offer a definite advantage.

So far, no process for the industrial preparation of cobalamins has mentioned the addition of precursors other than cobalt and 5,6-dimethyl-benzimidazole. Some strains which only produce cobalamins on media containing (R)-1-amino-2-propanol have recently been described (Crouzet et al., 1990, Grabau et al., 1992). (R)-1-Amino-2-propanol could, therefore, be used for improving the production of cobalamins. However, its use for a possible industrial fermentation is elaborate and expensive since, on the one hand, (R)-1-amino-2-propanol is an irritant and volatile product and, on the other hand, it can inhibit growth of the microorganism. It would be particularly advantageous, therefore, to find another precursor of the (R)-1-amino-2-propanol residue of cobalamins which does not suffer from these drawbacks. In this regard, a pathway for biosynthesizing (R)-1-amino-2-propanol from L-threonine via aminoacetone has been described in certain microorganisms. However, L-threonine does not complement the abovementioned strains.

More generally, it can be advantageous, for improving the production of cobalamins, to increase the quantity of their precursors in the medium, in particular if these precursors are limiting. This approach can be effected either by adding the limiting precursor, or one of its derivatives or analogues, directly to the medium, or by amplifying the in-situ synthesis of this precursor in the producer strain using genetic techniques, in particular recombinant DNA technology.

To that end, knowledge of the biosynthetic pathways of the cobalamins, and of their precursors, is a key step for improving the production of cobalamins.

Thus, most of the steps in the pathway for biosynthesizing vitamin B12 have recently been characterized in *Pseudomonas denitrificans* (Blanche et al., 1995). No less than 22 cob genes involved in cobalamin biosynthesis have been isolated and the functions of the majority of the polypeptides encoded by these genes have been identified.

Other genes which are probably involved in the biosynthesis of cobalamins, or of their precursors, have been isolated from other microorganisms. The function of some of these genes is not known. Only the precise determination of their role or of their effect would enable an application to be found for them. Thus, a DNA fragment carrying at least one gene required for forming the photosynthetic apparatus in a facultative photosynthetic bacterium, *Rhodobacter capsulatus*, has recently been sequenced (Pollich et al., 1993, Pollich et al., 1995a). It has been suggested that 5 of the 8 genes isolated are cobalamin biosynthesis genes because of their strong homology with 5 of the abovementioned 22 cob genes of *P. denitrificans*. By contrast, it has not been possible directly to assign any precise function to the 3 remaining genes, i.e. the genes bluB, bluE and bluF. The bluB, bluE and bluF genes, including their promoter sequences, have been sequenced and described in Pollich et al., 1995a.

According to the present invention, a novel precursor of cobalamin has been discovered. Thus, the present invention has made it possible to obtain an improvement in cobalamin production using media which contain O-phospho-L-threonine. This cobalamin precursor, which has not hitherto been described, has a role which is comparable to that of another, already known, precursor, i.e. (R)-1-amino-2-propanol. However, O-phospho-L-threonine possesses the advantage, as compared with (R)-1-amino-2-propanol, of not being toxic and of being a product which is easy to handle. Furthermore, its effectiveness in improving cobalamin production can be more than 1000 times greater than that of (R)-1-amino-2-propanol.

The present invention also relates to the use of a DNA fragment from *Rhodobacter capsulatus* for improving cobalamin production or for obtaining or augmenting the in-situ synthesis of O-phospho-L-threonine or 5,6-dimethylbenzimidazole by a given cell.

The present invention has made it possible to obtain an improvement in cobalamin production using media which do not contain (R)-1-amino-2-propanol or O-phospho-L-threonine by means of employing a DNA fragment which carries, in particular, the bluE and bluF genes of *Rhodobacter capsulatus*.

Finally, the present invention has made it possible to obtain an improvement in cobalamin production on media which do not contain 5,6-dimethyl-benzimidazole by means of introducing a DNA fragment which carries, in particular, the bluB gene of *Rhodobacter capsulatus*.

The present invention relates to a process for biosynthesizing cobalamins by fermenting a prokaryotic microorganism which produces cobalamin, characterized in that:

a microorganism is used which is transformed with at least one DNA fragment encoding an enzyme involved in a pathway for biosynthesizing O-phospho-L-threonine and the said microorganism is cultured under conditions which enable the said enzyme to be expressed and cobalamin to be produced; and/or O-phospho-L-threonine is added to the culture medium of the said microorganism; or an aerobic microorganism is used which is transformed with at least one DNA fragment encoding an enzyme involved in a pathway for biosynthesizing 5,6-dimethylbenzimidazole and the said microorganism is cultured aerobically under conditions which enable the said enzyme to be expressed and cobalamin to be produced.

The microorganism may harbour endogenously a gene such as characterized above. In this case, the process according to the invention enables the enzyme to be overexpressed. However, this type of gene may equally well not be present endogenously in the said microorganism.

"DNA fragment encoding an enzyme involved in a pathway for biosynthesizing O-phospho-L-threonine or 5,6-dimethylbenzimidazole" is understood to mean that expression of the said DNA fragment results in synthesis of O-phospho-L-threonine or 5,6-dimethyl-benzimidazole in the cell, possibly followed by release into the culture medium.

The culture can be performed as a batch culture or as a continuous culture and the cobalamins can be purified by means of methods which are already employed at the industrial level (Florent, 1986).

In one embodiment, a microorganism is used which is transformed with a DNA fragment which encodes a polypeptide involved in a pathway for biosynthesizing O-phospho-L-threonine and which encompasses the bluE and bluF genes of *Rhodobacter capsulatus,* or a fragment which is homologous, or hybridizes, with the said bluE and bluF genes and which has the same function, as the said genes, of encoding an enzyme which is involved in a pathway for biosynthesizing O-phospho-L-threonine.

In another embodiment, a microorganism is used which is transformed with a DNA fragment which encodes an enzyme involved in a pathway for biosynthesizing 5,6-dimethylbenzimidazole and which encompasses the bluB gene of *Rhodobacter capsulatus,* or a fragment which is homologous, or hybridizes, with the said bluB gene and which has the same function, as the said gene, of encoding an enzyme which is involved in a pathway for biosynthesizing 5,6-dimethylbenzimidazole.

The invention involves the use of a DNA fragment which is of natural, synthetic or recombinant origin and which is homologous. A fragment is understood to mean a fragment which results from the degeneracy of the genetic code or a fragment which exhibits a sequence homology of at least 25% and which encodes polypeptides having the same function.

Appropriately, a microorganism is used which is cultured aerobically and the said DNA fragment encodes an enzyme which is involved in a pathway for the aerobic biosynthesis of 5,6-dimethylbenzimidazole.

The present invention also relates to a process for preparing recombinant strains of a prokaryotic microorganism which produces cobalamin, characterized in that the said microorganism is transformed, by means of genetic manipulation techniques, with at least one DNA fragment which encodes an enzyme which is involved in a pathway for biosynthesizing O-phospho-L-threonine or 5,6-dimethylbenzimidazole as defined above.

The present invention also relates to the recombinant strains which are obtained by the strain-preparing process according to the present invention.

The present invention involves the use, in the processes according to the invention, of a recombinant DNA which contains at least one DNA sequence which encodes a said polypeptide and in which the said sequence(s) is/are placed under the control of expression signals.

In this respect, promoter regions can, in particular, be positioned 5' of the DNA sequence. These promoter regions can be homologous or heterologous in relation to the DNA sequence. In particular, it is possible to employ strong bacterial promoters, such as the tryptophan operon promoter Ptrp or the lactose operon promoter Plac of *E.coli* , the left-hand or right-hand promoter of bacteriophage lambda, the strong promoters of phages of bacteria such as the corynebacteria, the functional promoters in gram-negative bacteria, such as the Ptac promoter of *E.coli* , the PxylS promoter of the xylene catabolism genes of the TOL plasmid, and the amylase promoter Pamy of *Bacillus subtilis.* Mention may also be made of the promoters which are derived from yeast glycolytic genes, such as the promoters of the genes encoding phosphoglycerate kinase, glyceraldehyde-3-phosphate dehydrogenase, lactase or enolase, which promoters can be employed when the recombinant DNA has been introduced into a eukaryotic host. A ribosome binding site is also positioned 5' of the DNA sequence and it can be homologous or heterologous, such as the ribosome binding site of the cII gene of bacteriophage lambda.

Signals which are required for terminating transcription can be located 3' of the DNA sequence.

The recombinant DNA which is used in the processes according to the present invention can then be introduced directly into a host cell which is compatible with the chosen expression signals or be cloned into a plasmid vector in order to enable the DNA sequence in question to be introduced stably into the host cell.

The invention involves the use, in a known manner, of the plasmids which contain a DNA sequence encoding a said polypeptide. In a known manner, these plasmids also contain a functional replication system and a selection marker.

Different types of vector may be employed. Preference is given, within the context of the invention, to using vectors of the RK2 type, that is vectors which have an RK2 origin of replication. Mention may be made, as specific examples, of the RK2 vector (Saurugger et al., 1986), the pXL435 vector (Cameron et al., 1989), the pRK290 vector (U.S. Pat. No. 4,590,163; Ditta et al., 1985) and the pXL1635 vector (WO91/16439). A particularly advantageous vector is the pXL1635 vector. Other vectors are described in Application WO91/16439.

According to one embodiment, a microorganism is used which is transformed with a DNA fragment which encompasses a 6.8 kb BamHI fragment of the plasmid pER1 (FIG. 1), which fragment is described in the examples below and encodes the synthesis of the two precursors, O-phospho-L-threonine and 5,6-dimethylbenzimidazole.

In an embodiment which is more particularly appropriate for expressing a polypeptide involved in the synthesis of O-phospho-L-threonine, a DNA fragment is used which encompasses the 2.1 kb EcoRI/ClaI fragment of the plasmid pER2 (FIG. 2), which fragment is described in the examples which follow.

In an embodiment which is more particularly appropriate for expressing a polypeptide involved in the synthesis of O-phospho-L-threonine, a DNA fragment is used which encompasses the 1.6 kb EcoRI/EcoRV fragment of plasmid pER2 (FIG. 2), which fragment is described in the examples which follow.

In another embodiment, which is more particularly appropriate for expressing a polypeptide involved in the synthesis of 5,6-dimethylbenzimidazole, a DNA fragment is used which encompasses the 6.8 kb BamHI fragment of plasmid pER1, which fragment is described in the examples which follow.

The prokaryotic host microorganisms which may be used in accordance with the invention are, more specifically, the bacteria of the genus *E.coli, Pseudomonas denitrificans, Agrobacterium radiobacter, Agrobacterium tumefaciens*, or *Rhizobium melitoti* or else *Rhodobacter capsulatus*. Other bacteria are described in WO91/11518.

However, use will advantageously be made of a *P. denitrificans* or *A. radiobacter* bacterium.

Other advantages and characteristics of the present invention will come to light from the detailed description which follows.

Examples 1 and 2 describe how it is possible to obtain cobalamin production by adding O-phospho-L-threonine to the culture medium of a strain of *Pseudomonas denitrificans* or *Rhodobacter capsulatus*. Example 2 demonstrates how O-phospho-L-threonine can advantageously replace (R)-1-amino-2-propanol in the production media, in view of the fact that concentrations of (R)-1-amino-2-propanol which are at least 1000 times higher are required in order to obtain cobalamin production.

Example 2 also demonstrates that the region of the *Rhodobacter capsulatus* chromosome which harbours the bluE and bluF genes is involved in the synthesis of O-phospho-L-threonine. Example 3 describes the use of a DNA fragment from *Rhodobacter capsulatus* to construct plasmids which carry the bluE and bluF genes. This Example 3 demonstrates especially how these plasmids, once they have been introduced in strains whose cobalamin production is dependent on addition of (R)-1-amino-2-propanol or O-phospho-L-threonine, make it possible to obtain cobalamin production on media which do not contain (R)-1-amino-2-propanol or O-phospho-L-threonine. Example 4 demonstrates that the region of the *Rhodobacter capsulatus* chromosome which harbours the bluB gene is involved in the synthesis of 5,6-dimethylbenzimidazole.

BRIEF DESCRIPTION OF THE DRAWINGS

FIGS. 1 to 3 depict plasmids pER1, pER2 and pER3 respectively.

1. Strains and plasmids

Figure 1:
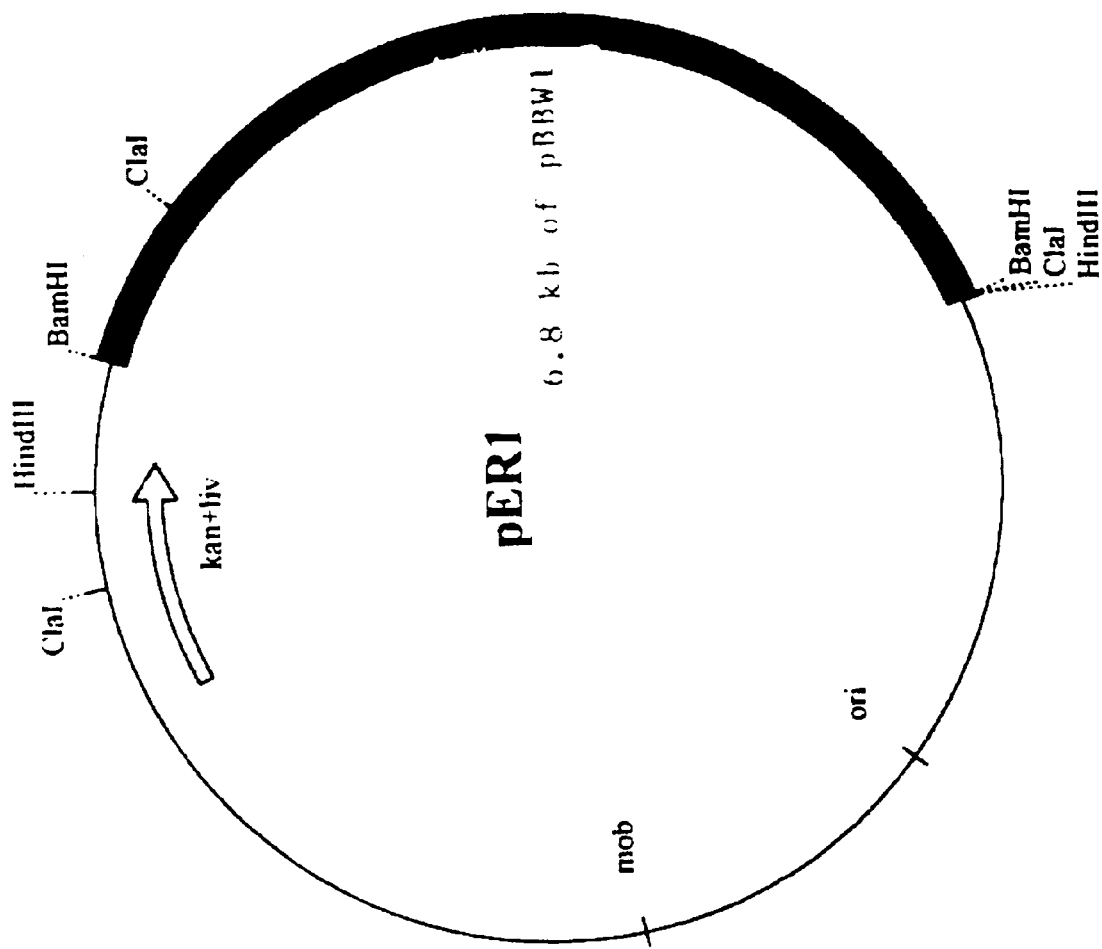
FIG. 1: restriction map of plasmid pER1

Strains AH2 and BB1 of *Rhodobacter capsulatus* (Pollich et al., 1995a) were constructed from strain 37b4 (DSM 938). Strain G2650 of *Pseudomonas denitrificans* was constructed from the strain SBL 27 Rifr by inserting the transposon $Tn^5$ (Crouzet et al., 1990). A strain G2650[Tet] was first of all constructed using a $Tn^5$ transposon carrying the gene for resistance to tetracycline. A strain G2650[Sp] was then constructed from strain G2650[Tet] by replacing the $Tn^5$ transposon gene for resistance to tetracycline with a gene for resistance to spectinomycin. Strain SBL 27 Rif$^r$ is derived from strain MB 580 (U.S. Pat. No. 3 018 225).

Plasmid pBBW1 was constructed using a DNA fragment from *Rhodobacter capsulatus* (Pollich et al., 1995a). Plasmid pAHW25 (Pollich and Klug, 1995a) was constructed from plasmid pBBW1.

2. Transformation techniques

*E.coli* strains are transformed by means of electroporation (Dower et al., 1988).

3. Conjugation techniques

Conjugations between *E.coli* strain S17-1 and the different *P. denitrificans* strains are carried out in accordance with a protocol which has been modified from that described by Simon and coworkers (Simon et al., 1986). The Pseudomonas strains may be transformed by any other genetic manipulation technique.

4. Preparation of the media for producing cobalamins

The medium which is used for the production of cobalamins by the *P. denitrificans* strains is the PS4 medium described by Cameron et al., 1989. One liter of PS4 medium, pH 7.2, contains sucrose (30 g), $(NH_4)_2HPO_4$ (3 g), sodium glutamate (6.3 g), $MnSO_4$ $H_2O$ (0.02 g), $ZnSO_47H_2O$ (0.02 g), $FeSO_47H_2O$ (0.03 g), $Na_2MoO_42H_2O$ (0.005 g), $CoCl_26H_2O$ (0.120 g), betaine (10 g), 5,6-dimethylbenzimidazole (0.045 g), $MgSO_47H_2O$ (1.5 g), NZ casamino acids (10 g), and KCl (0.9 g).

The medium which is used for the production of cobalamins by the *Rhodobacter capsulatus* strains is the RA medium described by Pollich, 1995b. One liter of RA medium, pH 6.9, contains L-malic acid (3 g), $MgSO_47H_2O$ (0.3 g), $CaCl_2$ (0.05 g), $(NH_4)_2SO_4$ (1.2 g), $K_2HPO_4$ (0.9 g), $KH_2PO_4$ (0.6 g), ferric citrate (750 µg), $MnCl_24H_2O$ (30 µg), $ZnCl$ (7.5 µg), LiCl (7.5 µg), KBr (3.75 µg), KI (3.75 µg), $CuSO_4$ (0.225 µg), $Na_2MoO_42H_2O$ (1.5 µg), $CoCl_26H_2O$ (7.5 µg), $SnCl_22H_2O$ (0.75 µg), $BaCl_2$ (0.75 µg), $AlCl_3$ (1.5 µg), $H_3BO_4$ (15 µg), EDTA (30 µg), nicotinic acid (0.0016 g), thiamine HCl (0.0032 g), and biotin (64 µg).

5. Assay of the cobalamins which are produced

The quantity of cobalamins produced is measured either by microbiological assay or by high performance liquid chromatography (HPLC).

Microbiological assay:

The quantity of cobalamins produced is measured by a semiquantitative method using the *E.coli* indicator strain 113-3, which is auxotrophic for vitamin B12 (Davis and Mingioli, 1950).

This indicator strain is a metE mutant of *E.coli* which thus possesses only one single homocysteine methyltransferase (EC 2.1.1.13) and which is B12-dependant. On minimal medium, it only requires the presence of vitamin B12 in order to grow. When this strain is included in an overlay of M9 minimal agar medium (Miller, 1972) (which only requires vitamin B12 in order to enable the strain to grow), it is possible to assay vitamin B12. Thus, if a sample of a solution containing vitamin B12 is deposited on the surface of the overlay, a growth halo is visible at the site of deposition after 16 h of incubation at 37° C. The vitamin B12 which is contained in the sample diffuses and enables the bacteria which are included in the agar to grow. The diameter of the growth halo is proportional to the concentration of B12 in the sample.

The samples are obtained by lysing the cells in accordance with the following protocol:

0.1 ml of a solution of (100 mM tris-HCl, pH=8, 20 mM EDTA, 200 g of sucrose/l) containing 24 mg of lysozyme (Boehringer Mannheim)/ml is mixed with 0.5 ml of the cell culture to be assayed. After incubating at 37° C. for 30 min, 60 µl of a 30 g/l solution of sodium dodecyl sulphate are added and the mixture is vortexed for a few seconds. 10 µl of the cell lysate which is obtained, or, where appropriate, of a 1/50 dilution, are deposited on the surface of the overlay.

HPLC assay:

The methods employed for assaying cobalamins by means of high performance liquid chromatography are those described by Blanche et al., 1990.

EXAMPLE 1
Effect of O-phospho-L-threonine on the production of cobalamins by a strain of Pseudomonas denitrificans.

The *Pseudomonas denitrificans* strain G2650 [Tet] is cultured, in a 100 ml Erlenmeyer flask, in 25 ml of PS4 medium containing 2 μg of tetracycline/ml. After fermenting at 30° C. for 24 h while shaking (250 rpm), 0.16 or 0.32 or 1.5 ml of a 10 g/l solution of O-phospho-L-threonine, corresponding to final concentrations of 66, 132 and 600 mg/l, respectively, are added, where appropriate, to the medium. The quantities of cobalamin which are produced under each of these conditions are assayed by HPLC after 148 h of fermentation. The results (Table 1) demonstrate that strain G2650 [Tet] does not produce vitamin B12 in PS4 medium. By contrast, the presence of O-phospho-L-threonine in the medium enables this same strain to produce B12. The quantity of vitamin B12 produced then increases as the quantity of O-phospho-L-threonine added is increased.

TABLE 1

| O-phospho-L-threonine added to the medium (mg/l) | 0 | 66 | 132 | 600 | 600 (added at t = 0) |
|---|---|---|---|---|---|
| B12 (mg/l) produced | 0 | 1.8 | 2.5 | 4.2 | 3.8 |

EXAMPLE 2
Comparison of the effects of O-phospho-L-threonine and (R)-1-amino-2-propanol on the production of cobalamins by a *Rhodobacter capsulatus* strain.

The *Rhodobacter capsulatus* strain AH2 is cultured, in a 100 ml Erlenmeyer flask, in 70 ml of RA medium in the presence of 10 μg of kanamycin/ml and different concentrations of O-phospho-L-threonine and (R)-1-amino-2-propanol. After fermenting at 30° C. for from 24 to 48 h while shaking (100 rpm), the quantity of cobalamins produced under the different conditions is measured by microbiological assay.

The results are shown in Table 2, in which "−" denotes the absence of the growth halo of the indicator strain and "+" the presence of a growth halo whose diameter is greater the greater the number of "+" symbols. These results demonstrate that, when cultured in RA medium, *R. capsulatus* strain AH2 does not produce vitamin B12. By contrast, in the presence of O-phospho-L-threonine or (R)-1-amino-2-propanol, this strain is able to produce vitamin B12. The results also demonstrate that it is necessary to add of the order of $6 \times 10^3$ times more (R)-1-amino-2-propanol in order to achieve the same result as that achieved with O-phospho-L-threonine.

TABLE 2

| Concentration of O-phospho-L-threonine in the medium | 10 nM | 25 nM | 50 nM | 100 nM | 250 nM |
|---|---|---|---|---|---|
| Production of B12 | − | + | ++ | +++ | ++++ |
| Concentration of (R)-1-amino-2-propanol in the medium | | 6 μM | 30 μM | 150 μM | 1.2 mM |
| Production of B12 | | − | − | − | + |

EXAMPLE 3
Effect of the presence of a DNA fragment derived from plasmid pBBW1 in strain G2650, which does not produce cobalamins.

3.1. Construction of plasmid PER1 (FIG. 1)

Plasmid pER1, of 17.4 kb, was constructed by cloning the 6.8 kb BamHI DNA fragment, which was purified from plasmid pBBW1 (Pollich and Klug, 1995), into the BamHI site of vector pXL435 (Cameron et al., 1989).

3.2. Introduction of plasmid PER1 into *P. denitrificans* strain G2650

Plasmid pER1 was initially introduced, by means of electroporation, into *E.coli* strain S17-1 and subsequently introduced into *P. denitrificans* strain G2650 [Tet] by conjugation with the *E.coli* S17-1 strain harbouring plasmid pER1. The transconjugants which were resistant to 50 μg of rifampicin/ml and 100 μg of lividomycin/ml were selected. 9 analysed clones harboured plasmid pER1.

A control G2650 [Tet] strain harbouring vector pXL435 alone was constructed in the same manner.

3.3. Cobalamin production by strain G2650 harbouring plasmid PER1.

G2650 [Tet] clones harbouring plasmid pER1, as well as 2 clones harbouring plasmid pXL435, were cultured in PS4 medium in the presence of rifampicin, tetracycline and lividomycin. After fermenting at 30° C. for 140 h with shaking (250 rpm), the quantity of cobalamins produced was measured by microbiological assay and by HPLC. The results are presented in Table 3.

TABLE 3

| | | B12, microbiological assay | B12 HPLC (mg/l) |
|---|---|---|---|
| G2650 [Tet] strains harbouring plasmid pER1 | 1 | ++ | 3 |
| | 2 | ++ | 3.5 |
| | 3 | ++ | 3.4 |
| | 4 | ++ | 3.2 |
| | 5 | ++ | 2.9 |
| | 6 | ++ | 3.9 |
| | 7 | ++ | 3.6 |
| | 8 | ++ | 3.3 |
| | 9 | ++ | 3.9 |
| G2650 [Tet] strains harbouring plasmid pXL435 | 1 | − | 0 |
| | 2 | − | 0 |
| Strain 62650 [Tet] | | − | 0 |

Whereas neither strain G2650 [Tet] nor this strain harbouring plasmid pXL435 produces vitamin B12 in PS4 medium, this same strain harbouring plasmid pER1 is able to produce B12 at a concentration of the order of 3.5 mg/l. The G2650 [Tet] strain harbouring plasmid pXL435, i.e. only the cloning vector which was used for constructing plasmid pER1, does not produce B12: it is therefore the presence of the 6.8 kb DNA fragment derived from plasmid pBBW1 which is responsible for producing the B12.

This 6.8 kb BamHI DNA fragment, which was purified from plasmid pBBW1, therefore confers on *P. denitrificans* strain G2650 [Tet] the ability to produce vitamin B12 in PS4 medium.

3.4. Subcloning

The regions of the 6.8 kb BamHI DNA fragment containing the bluE and bluF genes were subcloned into cloning vector pXL435, giving rise, by way of intermediate constructions, to the plasmids termed pER2 and pER3.

Figure 2:
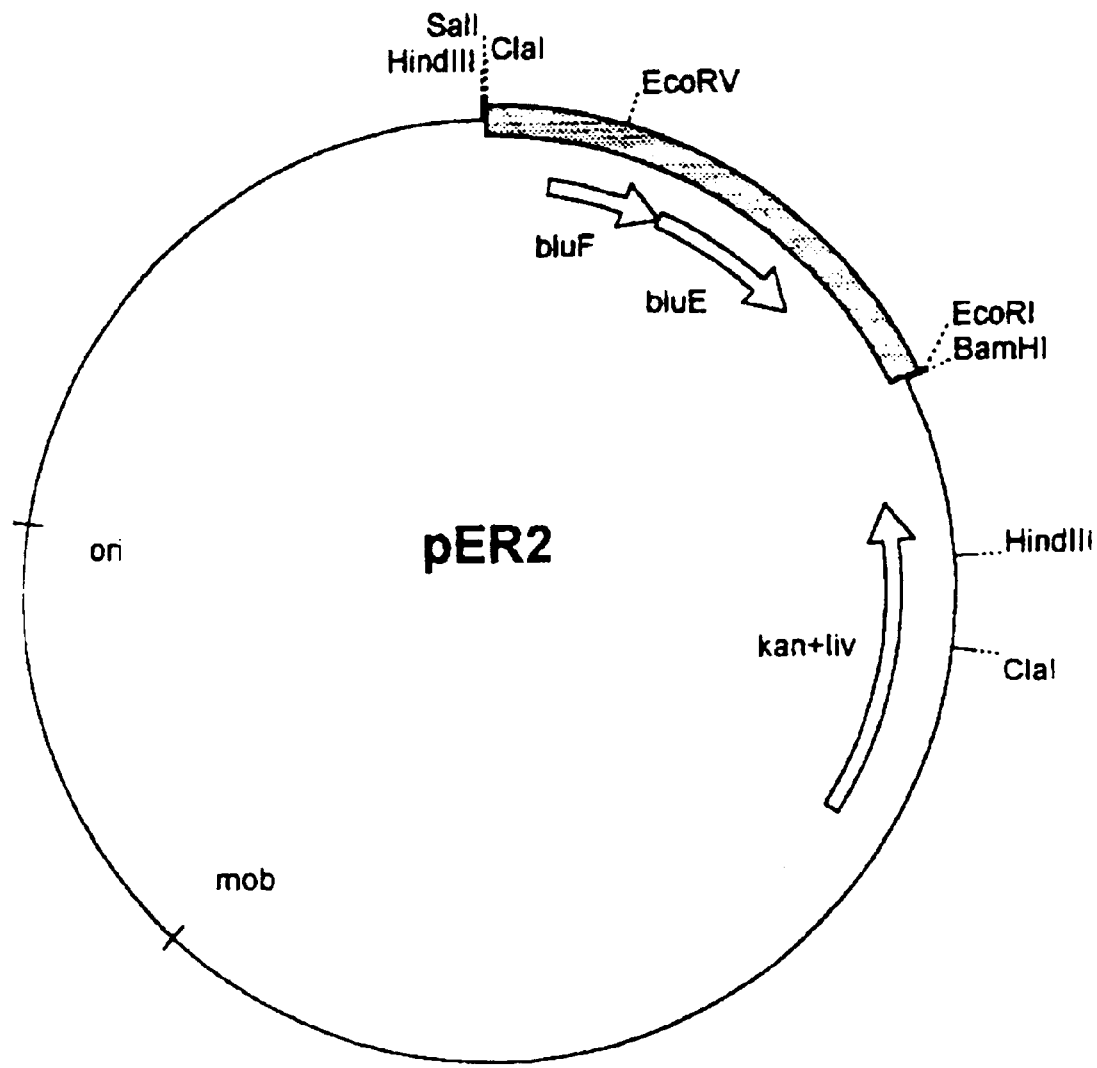
FIG. 2: restriction map of plasmid pER2

The 12.9 kb plasmid pER2 (FIG. 2) contains the 2.1 kb EcoRI/ClaI fragment, which was purified from plasmid pBBW1 and cloned into the pXL435 vector. Prior to that, this DNA fragment was cloned into the EcoRI/ClaI sites of plasmid pBluescript II SK+ (Stratagene) and then purified from this recombinant plasmid in the form of a BamHI/SalI DNA fragment for cloning into vector pXL435.

Figure 3:
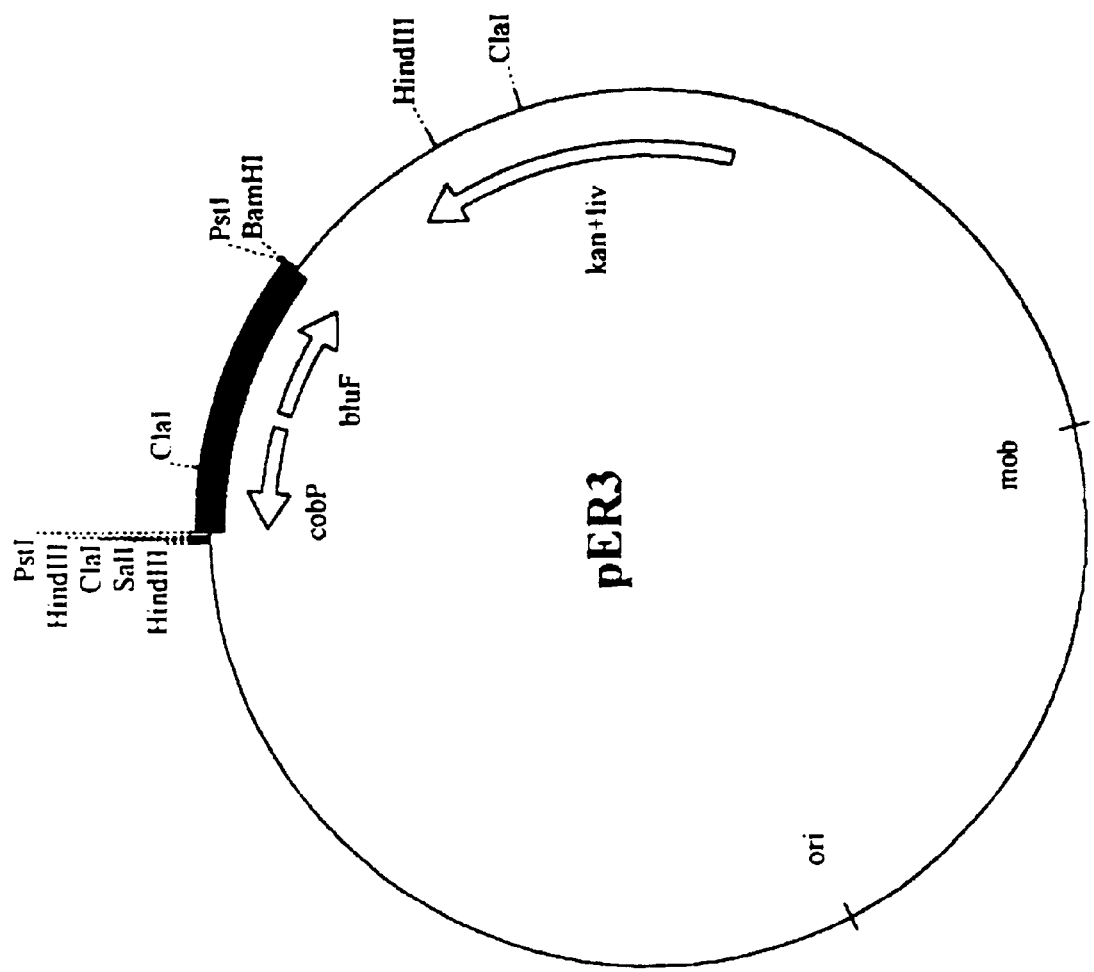
FIG. 3: restriction map of plasmid pER3

The 11.9 kb pER3 plasmid (FIG. 3) contains the 1.2 kb PstI fragment, which was purified from plasmid pBBW1 and cloned into the pXL435 vector. Prior to that, it was cloned into the PstI site of plasmid pBluescript II SK+ and was then purified from this recombinant plasmid in the form of a BamHI/SalI restriction fragment for cloning into vector pXL435.

Plasmid pAHW25 (Pollich and Klug, 1995a) contains the 1.6 kb EcoRI/EcoRV fragment, which was purified from plasmid pBBWI and cloned into the pRK415 vector (Keen at al., 1988): the bluE gene is then transcribed from the lac promoter of the vector.

Plasmids pER2 or pER3 were introduced into *P. denitrificans* strain G2650 [Tet] by conjugation with *E. coli* strain S17-1 harbouring these same plasmids. The G2650 [Tet] clones harbouring plasmids pER2, pER3 or pXL435 were cultured in 5 ml of PS4 medium in the presence of rifampicin, tetracycline and lividomycin. Plasmids pAHW25 and pRK415 were introduced into *P. denitrificans* G2650[Sp] strains by conjugation with *E. coli* strain S17-1 which harbours these same plasmids. The clones of G2650 [Sp] strains harbouring plasmids pAHW25 or pRK415 were cultured in 25 ml of PS4 medium in the presence of rifampicin, lividomycin and spectinomycin. After 140 h of fermentation at 30° C. with shaking (250 rpm), the quantity of cobalamins produced is measured by microbiological assay and by HPLC.

The results, which are presented in Table 4, demonstrate that only the clones of G2650 strains harbouring plasmids pER2 or pAHW25 are able to produce vitamin B12 in PS4 medium.

TABLE 4

|  |  | B12, microbiological assay | B12 by HPLC (mg/l) |
|---|---|---|---|
| Strain G2650 [Tet] |  | − | 0 |
| Strain G2650 [Sp] |  | − | 0 |
| G2650 [Tet] strains harbouring plasmid pXL435 | 1 | − | 0 |
|  | 2 | − | 0 |
|  | 3 | − | 0 |
| G2650[Tet] strains harbouring plasmid pER2 | 1 | ++ | 7.4 |
|  | 2 | ++ | 5.3 |
|  | 3 | ++ | 7.9 |
|  | 4 | ++ | 3.5 |
|  | 5 | ++ | 5.2 |
|  | 6 | ++ | 6.8 |
|  | 7 | ++ | 7.2 |
| G2650[Tet] strains harbouring plasmid pER3 | 1 | − | 0 |
|  | 2 | − | 0 |
|  | 3 | − | 0 |
|  | 4 | − | 0 |
|  | 5 | − | 0 |
|  | 6 | − | 0 |
|  | 7 | − | 0 |
|  | 8 | − | 0 |
| G2650[Sp] strains harbouring plasmid pRK415 | 1 | − | 0 |
|  | 2 | − | 0 |
|  | 3 | − | 0 |
|  | 4 | − | 0 |
| G2650[Sp] strains harbouring plasmid pAHW25 | 1 | ++ | 3.0 |
|  | 2 | ++ | 2.2 |
|  | 3 | ++ | 3.0 |
|  | 4 | ++ | 2.9 |
|  | 5 | ++ | 2.9 |
|  | 6 | ++ | 3.3 |
|  | 7 | ++ | 3.1 |
|  | 8 | ++ | 2.4 |

EXAMPLE 4

The bluB gene is involved in the biosynthesis of 5,6-dimethylbenzimidazole (DBI), a known precursor of B12.

*Rhodobacter capsulatus* strain BB1 is a mutant strain which was obtained by inserting an interposon into the bluB gene: the mutant strain is a bluB⁻ strain (Pollich et al., 1995). Strain BB1 is cultured in 70 ml of RA medium, in a 100 ml Erlenmeyer flask, in the presence of 10 μg of kanamycin/ml and of different concentrations of DBI. The quantities of cobalamins which are produced by this strain under the different conditions are measured by microbiological assay after 24 to 48 h of fermentation at 30° C. with shaking (100 rpm). The results, which are summarized in Table 5, demonstrate that mutant strain BB1, which does not produce B12 in RA medium alone, synthesizes this molecule when at least 14 nM of DBI are present in the medium. The bluB gene is therefore involved in the biosynthesis of 5,6-dimethylbenzimidazole.

TABLE 5

| Concentration of DBI in the medium, nM | 0 | 7 | 14 | 35 | 70 | 140 | 350 |
|---|---|---|---|---|---|---|---|
| Production of B12 | − | − | + | ++ | +++ | ++++ | +++++ |

REFERENCES

1. Davis B. D. and E. Mingioli (1950), J. Bacteriol., 60: 17–28
2. Dower W. J., J. F. Miller and C. W. Ragsdale (1988) Nucl. Acids Res., 16: 6127–6145 Ref M9
3. Sambrook J., E. F. Fritsch and T. Maniatis (1989) Molecular cloning, a laboratory manual, second edition
4. Simon R., M. O'C.onnell, M. Labes and A. Pühler (1986) Meth. In Enzymology, 118: 640–659
5. Blanche F., D. Thibaut, M. Couder, and J. C. Muller (1990), Anal. Biochem., 189: 24–29
6. Blanche F., B. Cameron, J. Crouzet, L. Debussche, D. Thibaut, M. Vuilhorgne, F. J. Leeper, and A. R. Battersby (1995) Angew. Chem. Int. Ed. Engl., 34: 383–411
7. Cameron B., K. Briggs, S. Pridmore, G. Brefort, and J. Crouzet (1989) J.Bacteriol., 171: 547–557
8. Crouzet J., L. Cauchois, F. Blanche, L. Debussche, D. Thibaut, M. C. Rouyez, S. Rigault, J. F. Mayaux, and B. Cameron (1990) J. Bacteriol., 172: 5968–5979
9. Grabau C., and J. R. Roth (1992) J. Bacteriol., 174: 2138–2144
10. Pollich M., S. Jock, and G. Klug (1993) Mol. Microbiol., 10: 749–757
11. Pollich M., and G. Klug (1995a) J. Bacteriol., 177: 4481–4487
12. Pollich M. (1995b) Dissertation, Ruprecht-Karls-Universität Heidelberg
13. Florent J., (1986), Vitamins, Biotechnology, vol. 4, VCH Verlagsgesellschaft mbH, Weinheim, In H.-J. Rehm and G. Reed (ed.), 115–158
14. Ditta G., Schmidhauser T., Yakobson E., Lu P., Liang X. W., Finlay D. R., Guiney D., and Helinski D., (1985), Plasmid, 13: 149–154.
15. Miller J. H., (1972), Experiments in Molecular Genetics, Cold Spring Harbor, N.Y.
16. Saurugger P. N., Hrabak O., Schwab H., and Lafferty R. N., (1986), J. Biotechnol. 4: 333–343
17. Keen N. T., S. Tamaki, D. Kobayashi and D. Trollinger (1988) Gene 70: 191–197

We claim:

1. A process for amplifying the biosynthesis of cobalamins in a prokaryotic microorganism, which produces cobalamins, comprising the following method steps:

(i) preparing culture medium comprising O-phospho-L-threonine; and (ii) culturing said prokaryotic microorganism in said culture medium under conditions appropriate for the production of cobalamins.

2. A process for amplifying the biosynthesis of cobalamins in a prokarotic microorganism, which produces cobalamins, comprising the following method steps:

(i) transforming said prokaryotic microorganism with a DNA fragment which encodes a polypeptide involved in a pathway for biosynthesizing O-phospho-L-threonine and which comprises the bluE and bluF genes of *Rhodobacter capsulatus;* and (ii) culturing said prokaryotic microorganism under conditions appropriate for the production of cobalamins.

3. The process of claim 2 wherein said DNA fragment comprises the 2.1 kb EcoR1/Clal fragment of plasmid pER2.

4. A process for amplifying the biosynthesis of cobalamins in a prokaryotic microorganism, which produces cobalamins, comprising the following method steps:

(i) transforming said prokaryotic microorganism with the EcoRI/EcoRV fragment of plasmid pAHW25 or of plasmid pER2; and (ii) culturing said prokaryotic microorganism under conditions appropriate for the production of cobalamins.

5. A process for amplifying the biosynthesis of cobalamins in a prokaryotic microorganism, which produces cobalamins, comprising the following method steps:

(i) transforming said prokaryotic microorganism with a DNA fragment which encodes a polypeptide involved in a pathway for biosynthesizing 5,6-dimethylbenzimidazole and which comprises the blau gene of *Rhodobacter capsulatus;* and (ii) culturing said prokaryotic microorganism under conditions appropriate for the production of cobalamins.

6. The process of claim 2 wherein said DNA fragment comprises the 6.8 kb BamH1 fragment of plasmid pER1.

7. The process of claim 5 wherein said DNA fragment comprises the 6.8 kb BamH1 fragment of plastrd pER1.

8. The process of any one of claims 1, 2, 3, 4, 5, or 7 wherein said prokaryotic microorganism is a strain of *Psuedornonas denitrificans* or a strain of *Agrobacterium radiobacter.*

9. A process for preparing recombinant strains of a prokaryotic microorganism which produces cobalamin, wherein said process comprises:

transforming said prokaryotic microorganism, by means of genetic manipulation techniques, with at least one of the following:

a. a DNA fragment which encodes a polypeptide involved in a pathway for biosynthesizing O-phospho-L-theronine and which comprises the bluE and bluF genes of *Rhodobacter capsulatus;* or b. a DNA fragment which encodes a polypeptide involved in a pathway for biosynthesizing 5,6-dimethylbenzimidazle and which comprises the bluB gene of *Rhodobacter capsulatus* and wherein said prokaryotic microorganism is selected from the group consisting of a strain of *Pseudomonas denitirifcans,* a strain of *Agrobacteriurn radiobacter, Agrobacterium tumefaciens, Escherichia coli,* and *Rhizobium melitoti.*

10. A recombinant rnicroorganism obtained by the process according to claim 9.

11. A process for preparing vitamin $B_{12}$ comprising the method steps of claims 1, 2, or 5, and said process additionally comprising the following method step;

(iii) recovering vitamin $B_{12}$.

12. The process of claim 11 wherein said prokaryotic microorganism is a strain of *Psuedornonas denitrificans* or strain of *Agrobacterium radiobacter.*

* * * * *

UNITED STATES PATENT AND TRADEMARK OFFICE
CERTIFICATE OF CORRECTION

PATENT NO. : 6,156,545
DATED : December 5, 2000
INVENTOR(S) : Francis Blanche et al.

It is certified that error appears in the above-identified patent and that said Letters Patent is hereby corrected as shown below:

Column 5,
Line 61, after "(Pollich et al., 1995a)" insert -- , which was deposited with the Collection National de Cultures de Microorganisms (CNCM), Institut Pasteur, 25 rue du Docteur Roux, F-75724 Paris Cédex 15, FRANCE on January 15, 2001 (accession number I-2611) --.

Column 8,
Line 5, after "(Cameron et al., 1989)" insert -- , which was deposited with the Collection National de Cultures de Microorganisms (CNCM), Institut Pasteur, 25 rue du Docteur Roux, F-75724 Paris Cédex 15, FRANCE on January 15, 2001 (accession number I-2612) --.

Signed and Sealed this

Ninth Day of October, 2001

Attest:

*Nicholas P. Godici*

NICHOLAS P. GODICI
*Attesting Officer*   *Acting Director of the United States Patent and Trademark Office*